US009049995B2

(12) United States Patent
Blomqvist et al.

(10) Patent No.: US 9,049,995 B2
(45) Date of Patent: Jun. 9, 2015

(54) SYSTEM AND METHOD FOR DETECTING PULMONARY CONGESTION BASED ON STROKE VOLUME USING AN IMPLANTABLE MEDICAL DEVICE

(75) Inventors: Andreas Blomqvist, Taby (SE); Alex Soriano, Ventura, CA (US)

(73) Assignee: PACESETTER, INC., Sylmar, CA (US)

( * ) Notice: Subject to any disclaimer, the term of this patent is extended or adjusted under 35 U.S.C. 154(b) by 543 days.

(21) Appl. No.: 13/349,505

(22) Filed: Jan. 12, 2012

(65) Prior Publication Data

US 2013/0184545 A1    Jul. 18, 2013

(51) Int. Cl.
| A61B 5/02 | (2006.01) |
| A61B 5/0215 | (2006.01) |
| A61N 1/365 | (2006.01) |
| A61B 5/00 | (2006.01) |
| A61B 5/053 | (2006.01) |
| A61B 5/042 | (2006.01) |
| A61B 5/046 | (2006.01) |
| A61B 5/0464 | (2006.01) |

(52) U.S. Cl.
CPC .......... *A61B 5/0215* (2013.01); *A61N 1/36521* (2013.01); *A61N 1/36564* (2013.01); *A61B 5/686* (2013.01); *A61B 5/042* (2013.01); *A61B 5/046* (2013.01); *A61B 5/0464* (2013.01); *A61B 5/0538* (2013.01)

(58) Field of Classification Search
USPC .................. 600/481, 485, 486, 488, 504–508
See application file for complete search history.

(56) References Cited

U.S. PATENT DOCUMENTS

| 5,328,460 | A | 7/1994 | Lord et al. |
| 6,480,733 | B1 | 11/2002 | Turcott |
| 6,572,557 | B2 | 6/2003 | Tchou et al. |
| 6,643,548 | B1 | 11/2003 | Mai et al. |
| 6,741,885 | B1 | 5/2004 | Park et al. |
| 6,748,261 | B1 | 6/2004 | Kroll et al. |
| 7,024,244 | B2 * | 4/2006 | Muhlenberg et al. ........... 607/23 |
| 7,139,609 | B1 | 11/2006 | Min et al. |
| 7,142,911 | B2 | 11/2006 | Boileau et al. |
| 7,200,439 | B2 * | 4/2007 | Zdeblick et al. ................ 607/17 |

(Continued)

FOREIGN PATENT DOCUMENTS

| EP | 1698276 A1 | 9/2006 |
| EP | 1709993 A1 | 10/2006 |

OTHER PUBLICATIONS

Alderman et al., Evaluation of the Pulse-Contour Method of Determining Stroke Volume in Man, Circulation: Journal of the American Heart Association, Circulation. 1972;46:546-558.*

(Continued)

*Primary Examiner* — Michael D'Angelo

(57) ABSTRACT

Techniques are provided for detecting pulmonary congestion based on an increase in right ventricular (RV) stroke volume over left ventricular (LV) stroke volume. In one example, the device generates an index based on accumulated differences between RV stroke volume and LV stroke volume while RV stroke volume exceeds LV stroke volume, such that the index is indicative of an ongoing imbalance between RV and LV stroke volume. The index is compared to a suitable threshold to detect a severe imbalance indicative of pulmonary edema. Additionally, techniques are described for estimating RV and LV stroke volumes based on pulmonary artery pressure, left atrial pressure, aortic pressure, LV strain or on various intracardiac or extracardiac impedance measurements.

26 Claims, 10 Drawing Sheets

(56) References Cited

U.S. PATENT DOCUMENTS

| | | | |
|---|---|---|---|
| 7,267,649 B2* | 9/2007 | Zdeblick et al. | 600/301 |
| 7,272,443 B2 | 9/2007 | Min et al. | |
| 7,437,192 B2 | 10/2008 | Gill et al. | |
| 7,488,290 B1* | 2/2009 | Stahmann et al. | 600/485 |
| 7,507,208 B2* | 3/2009 | Bennett et al. | 600/485 |
| 7,621,036 B2 | 11/2009 | Cros et al. | |
| 7,628,757 B1 | 12/2009 | Koh | |
| 7,689,283 B1* | 3/2010 | Schecter | 607/18 |
| 7,704,209 B2* | 4/2010 | Bennett et al. | 600/465 |
| 7,738,958 B2* | 6/2010 | Zdeblick et al. | 607/17 |
| 7,805,194 B1 | 9/2010 | Schecter | |
| 7,917,194 B1 | 3/2011 | Reed et al. | |
| 7,925,348 B1 | 4/2011 | Bornzin et al. | |
| 8,019,409 B2 | 9/2011 | Rosenberg et al. | |
| 8,021,307 B2 | 9/2011 | White et al. | |
| 8,463,361 B2* | 6/2013 | Tupin, Jr. | 600/427 |
| 8,679,026 B2* | 3/2014 | Blomqvist | 600/486 |
| 2003/0055345 A1 | 3/2003 | Eigler et al. | |
| 2003/0199779 A1* | 10/2003 | Muhlenberg et al. | 600/513 |
| 2004/0215049 A1* | 10/2004 | Zdeblick et al. | 600/16 |
| 2004/0220637 A1* | 11/2004 | Zdeblick et al. | 607/17 |
| 2005/0203429 A1* | 9/2005 | Judy | 600/508 |
| 2005/0216067 A1 | 9/2005 | Min et al. | |
| 2006/0155204 A1* | 7/2006 | Wariar et al. | 600/528 |
| 2006/0167361 A1* | 7/2006 | Bennett et al. | 600/486 |
| 2006/0224190 A1 | 10/2006 | Gill et al. | |
| 2006/0287602 A1 | 12/2006 | O'Brien et al. | |
| 2007/0219591 A1* | 9/2007 | Zdeblick et al. | 607/17 |
| 2008/0097227 A1* | 4/2008 | Zdeblick et al. | 600/486 |
| 2008/0228238 A1* | 9/2008 | Libbus | 607/44 |
| 2008/0243006 A1* | 10/2008 | Benneth et al. | 600/485 |
| 2008/0294209 A1 | 11/2008 | Thompson et al. | |
| 2009/0118627 A1* | 5/2009 | Stahmann et al. | 600/486 |
| 2009/0209876 A1* | 8/2009 | Bennett et al. | 600/513 |
| 2009/0275854 A1* | 11/2009 | Zielinski et al. | 600/547 |
| 2010/0022911 A1* | 1/2010 | Wariar et al. | 600/561 |
| 2010/0030087 A1 | 2/2010 | Hettrick et al. | |
| 2010/0069778 A1 | 3/2010 | Bornzin et al. | |
| 2010/0106210 A1 | 4/2010 | Hedberg et al. | |
| 2010/0113944 A1* | 5/2010 | Min et al. | 600/486 |
| 2010/0262206 A1* | 10/2010 | Zdeblick et al. | 607/24 |
| 2010/0286535 A1* | 11/2010 | Blomqvist | 600/485 |
| 2010/0305641 A1 | 12/2010 | Pillai et al. | |
| 2011/0028855 A1 | 2/2011 | Blomqvist | |
| 2011/0125049 A1 | 5/2011 | Nabutovsky et al. | |
| 2011/0125207 A1 | 5/2011 | Nabutovsky et al. | |
| 2011/0144508 A1 | 6/2011 | Blomqvist et al. | |
| 2011/0184301 A1 | 7/2011 | Holmstrom et al. | |
| 2011/0196440 A1* | 8/2011 | Koh | 607/15 |
| 2011/0208077 A1 | 8/2011 | Soriano et al. | |
| 2011/0301473 A1* | 12/2011 | Wariar et al. | 600/486 |
| 2011/0319776 A1* | 12/2011 | Sweeney et al. | 600/509 |
| 2012/0022384 A1* | 1/2012 | Teixeira | 600/509 |
| 2012/0277545 A1* | 11/2012 | Teixeira | 600/301 |
| 2012/0296219 A1* | 11/2012 | Chon et al. | 600/479 |

OTHER PUBLICATIONS

Adamson, Philip B. et al., "CardioMEMS Heart Sensor Allows Monitoring of Pressures to Improve Outcomes in NYHA Class III Heart Failure Patients (Champion) Trial: Impact of Hemodynamic Guided Care on Patients With Preserved Ejection Fraction," J Cardiac Failure. Nov. 2010;16(11):913.

Abraham, William T. et al., "Wireless pulmonary artery haemodynamic monitoring in chronic heart failure: a randomised controlled trial." The Lancet. Feb. 2011:377(9766):658-666.

Alderman, Edwin L. MD et al., "Evaluation of the Pulse-Contour Method of Determining Stroke Volume in Man," Circulation. 1972;46:546-558.

Bennett, Susan J. DNS, RN et al., "Cost of hospitalizations for heart failure: Sodium retention versus other decompensating factors," Heart Lung. Mar.-Apr. 1999;28(2):102-109.

Chan, Wandy et al., "Effects of CRT Interval Optimization on Continuous Left Atrial Pressure Waveforms in Ambulant Heart Failure Patients and Inter-Patient Repeatability," J Cardiac Failure. Aug. 2011;17(8 Supp):S56.

Lloyd-Jones, Donald et al. "Heart Disease and Stroke Statistics—2010 Update. A Report from the American Heart Association (Statistics Committee and Stroke Staistics Subcommittee," Circulation. 2010:121(7):e46-e215.

* cited by examiner

SYSTEM AND METHOD FOR DETECTING PULMONARY CONGESTION BASED ON STROKE VOLUME USING AN IMPLANTABLE MEDICAL DEVICE

FIELD OF THE INVENTION

The invention generally relates to implantable medical devices, such as pacemakers, implantable cardioverter/defibrillators (ICDs) and cardiac resynchronization therapy (CRT) devices and in particular to techniques for use by such devices within heart failure patients to detect pulmonary edema.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Pulmonary edema occurs when the alveoli of the lungs fill with fluid instead of air, preventing oxygen from being absorbed into the bloodstream. That is, when a diseased or overworked left ventricle is no longer able to pump enough of the blood it receives from the lungs, pressure thereby increases inside the left atrium and then in the pulmonary veins and capillaries, causing fluid to be pushed through the capillary walls into the air sacs. This can cause severe respiratory problems and, left untreated, can be fatal. Note that pulmonary edema can also arise due to other factors besides heart failure, such as infections. Pulmonary edema due to heart failure may be specifically referred to as cardiogenic pulmonary edema. Herein, for brevity, the term pulmonary edema will be used to refer to cardiogenic pulmonary edema.

In general, whenever the right ventricle pumps more blood than the left ventricle is capable of pumping (for whatever reason), pulmonary congestion will arise. It would be desirable to exploit this insight to provide techniques for detecting pulmonary congestion and edema, and it is to that end that the invention is generally directed.

SUMMARY OF THE INVENTION

In accordance with an exemplary embodiment of the invention, techniques are provided for use with an implantable medical device for implant within a patient to detect an indication of pulmonary edema or pulmonary congestion. Briefly, the device detects values representative of right ventricular (RV) stroke volume within the patient and also detects values representative of left ventricular (LV) stroke volume within the patient. The device then evaluates differences between the RV stroke volume values and the LV stroke volume values and detects the indication of pulmonary edema/congestion based on the differences. For example, the device may generate an index based on accumulated differences between RV stroke volume and LV stroke volume while RV stroke volume exceeds LV stroke volume. The index is indicative of an imbalance between RV and LV stroke volume. The larger the index, the greater the imbalance between RV and LV stroke volume and the more likely there is pulmonary congestion and edema. That is, the device exploits the recognition that whenever the RV pumps more blood than the LV is capable of pumping, there will be pulmonary congestion. The accumulated difference index is compared to a suitable threshold to detect significant pulmonary congestion.

In an illustrative embodiment, where the device is a pacemaker, ICD or CRT equipped with various pressure sensors on its pacing/sensing leads, the device uses a pressure sensor mounted in the pulmonary artery to estimate RV stroke volume ($SV_{RV}$) by calculating:

$$SV = K \cdot \sqrt{P_{md}} \cdot \left(1 + \frac{S_a}{D_a}\right)$$

where SV is the RV stroke volume ($SV_{RV}$), $P_{md}$ is a mean pressure difference in the pulmonary pressure signal between systole and diastole (such as between the last 80 milliseconds (ms) of systole and the last 80 ms of diastole), $S_a$ is an integrated systolic pressure value derived from pulmonary pressure values above a predetermined pressure and extending over a period of time around systole (such as values above 20 mmHg from a point 80 ms before the onset of systole to a point 80 ms before the onset of diastole), $D_a$ is an integrated diastolic pressure value based on pulmonary pressure values above the predetermine pressure and extending over a period of time around systole (such as above 20 mmHg from a point 80 ms before the onset of diastole to a point 80 ms before the onset of systole) and K is a predetermined conversion factor or calibration coefficient for use with RV stroke volume. Alternatively, the device estimates $SV_{RV}$ based on intracardiac impedance signals derived by injecting current along a right atrial (RA) ring—RV ring vector and measuring impedance RA tip—RV tip. Peak-to-peak variations in the measured impedance are generally proportional to RV stroke volume and can be converted to RV stroke volume values using suitable conversion factors or coefficients. For example, amplitude changes of the aforementioned impedance configuration can be used to reflect RV stroke volume through a linear relationship (i.e. relative amplitude changes are the same as relative SV changes subject to conversion value for converting to milliliters (ml).) In this manner, intracardiac impedance is used as a proxy for RV stroke volume.

In the illustrative embodiment, the device also uses one or more proxies for estimating LV stroke volume ($SV_{LV}$) For example, $SV_{LV}$ can be estimated based on extracardiac impedance signals measured along a vector between a superior vena cava (SVC) coil electrode and the device housing (or can) electrode. Certain variations in the measured extracardiac impedance values are then converted to LV stroke volume values using suitable conversion factors. As another example, the device detects values representative of left atrial pressure (LAP) using a suitable sensor or proxy and then estimates LV stroke volume based on a maximum positive rate of change in the LAP values using suitable conversion factors. In still another example, the device uses an LV strain gauge sensor to detect values representative of changes in the curvature of the ventricular epicardium, which are proportional to LV volume. Changes in the strain gauge output values are converted to yield an estimate of LV stroke volume using suitable conversion factors. In yet other examples, the device exploits mixed venous oxygen saturation ($S_VO_2$)-based techniques to estimate LV stroke volume using Fick's principle or uses an aortic pressure sensor or proxy (if available) to estimate LV stroke volume in the same manner by which RV stroke volume is estimated from pulmonary artery pressure.

Within the illustrative embodiment, once both the RV and LV stroke volumes have been detected or estimated, the device then sums or accumulates differences between RV stroke volume and LV stroke volume during a period of time while the RV stroke volume exceeds the LV stroke volume by at least a minimal amount ($\delta$). In one example, this is performed by calculating a difference value $\Delta$ between RV and LV stroke volume and then iteratively accumulating or summing $\Delta$ over time using $\Delta'=\Delta'+\Delta$. The accumulated value ($\Delta'$) is compared against an accumulation threshold $\Theta$ and, if it exceeds the threshold, an alarm is generated to warn the patient or caregiver of possible pulmonary edema so that the condition may be addressed before hospitalization is required. Additionally, the device also tracks the amount of time (T) that RV stroke volume exceeds LV stroke volume for comparison against a time threshold ($\Gamma$) and if it exceeds the time threshold, an alarm is also generated to indicate possible pulmonary edema. Other actions can additionally be taken, such as recording suitable diagnostics for clinician review, controlling device therapy or titrating diuretics via an implanted drug pump (if one is provided.) Note that the accumulated value $\Delta'$ may also be referred to as an edema index $\epsilon_i$.

System and method examples of various embodiments of the invention are described herein.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
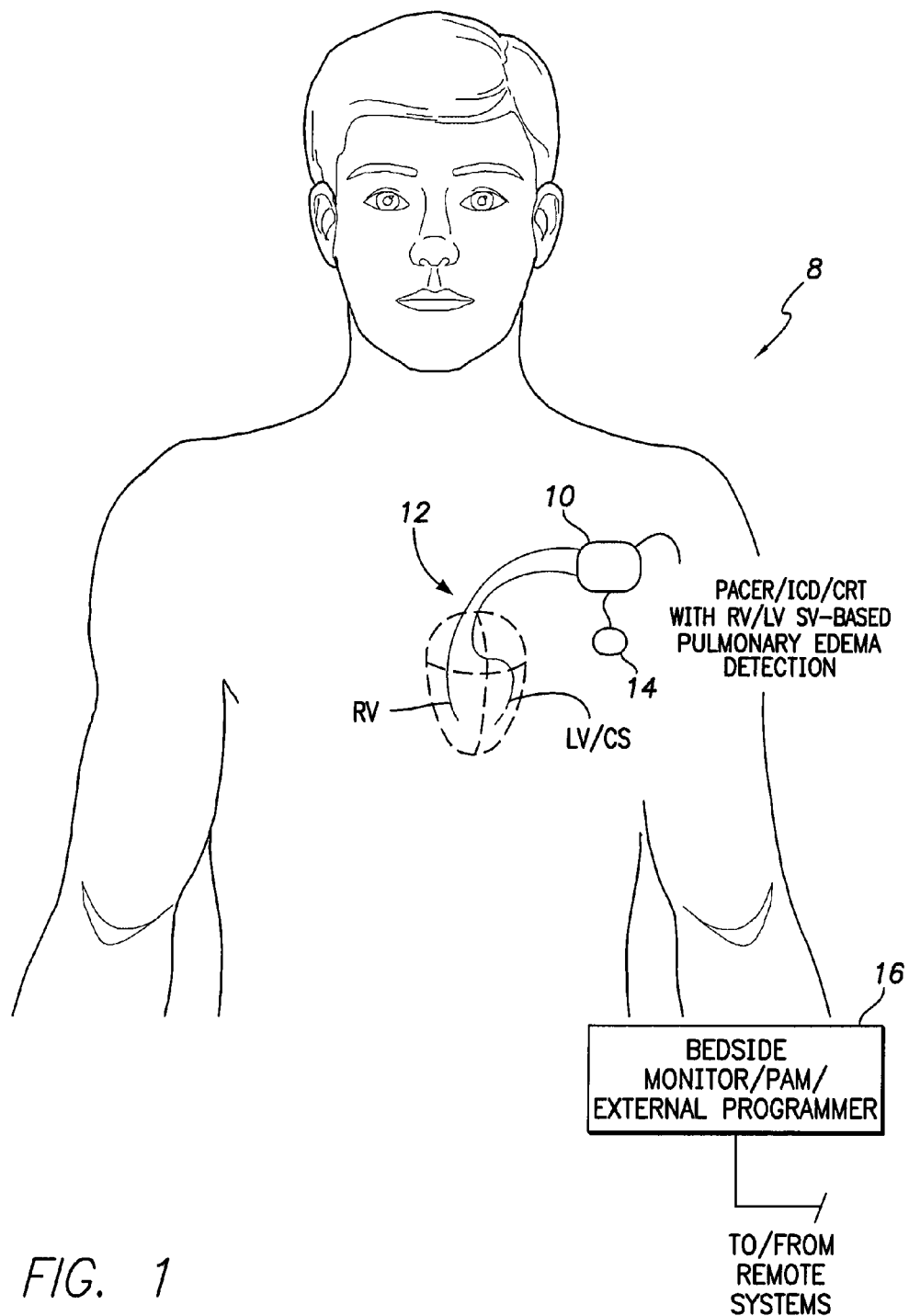
FIG. 1 illustrates pertinent components of an implantable medical system having a pacemaker or ICD capable of detecting pulmonary fluid congestion and/or edema within a patient based on RV and LV stroke volume.
Figure 8:
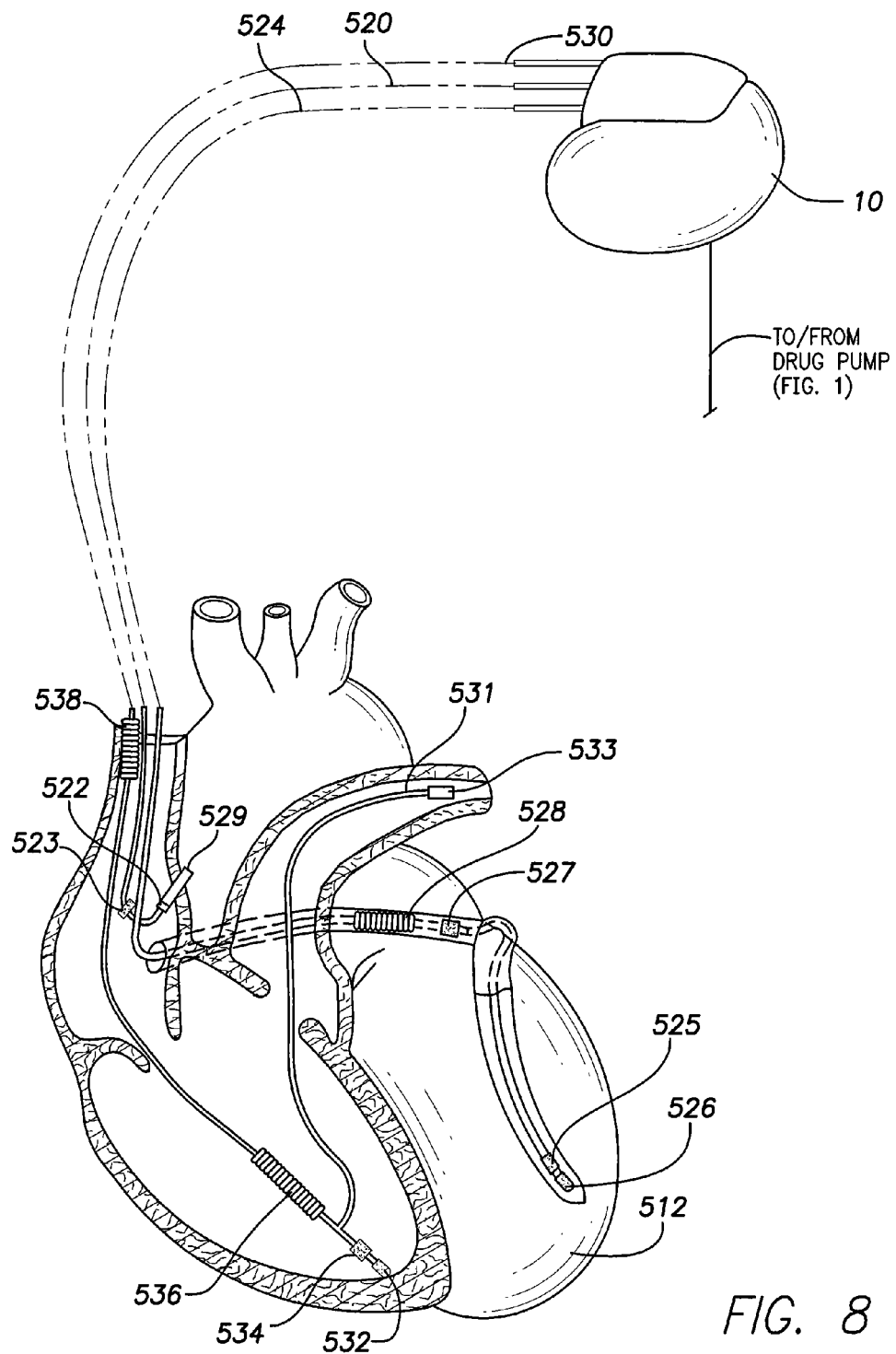
FIG. 8 is a simplified, partly cutaway view, illustrating the pacer/CRT of FIG. 1 along with a set of leads implanted on or in the heart of the patient.

FIG. 1 illustrates an implantable medical system 8 capable of detecting pulmonary congestion and edema based on a comparison of RV and LV stroke volumes, i.e. the system is equipped with an RV/LV stroke volume-based edema detection system. To this end, medical system 8 includes a pacer/ICD/CRT 10 or other cardiac rhythm management device equipped with one or more cardiac sensing/pacing leads 12 implanted within the heart of the patient. In FIG. 1, two exemplary leads are shown: an RV lead and an LV lead implanted via the coronary sinus (CS). An RA lead may also be provided. Although not shown in FIG. 1, one or more pressure sensors or transducers may be provided, particularly sensors for sensing pressure in the pulmonary artery, left atrium and/or aorta. A more complete set of leads is illustrated in FIG. 8, including an RV lead having a pulmonary artery sensor and an RA lead having a transseptally-implanted LAP sensor. Other sensors that may be exploited are shown schematically in FIG. 9. Although identified as a "pacer/ICD/CRT" within FIG. 1, it should be understood that device 10 can be any suitably-equipped implantable medical device, such as a standalone pacemaker, ICD or CRT device, including CRT-D and CRT-P devices. In the following, for brevity, device 10 will be referred to simply as a pacer/CRT.

In some examples, the system is equipped to automatically titrate diuretics in response to detection of pulmonary congestion using an implanted or subcutaneous drug pump or other drug dispensing device 14. Implantable drug pumps for use in dispensing medications are discussed in U.S. Pat. No. 5,328,460 to Lord et al., entitled "Implantable Medication Infusion Pump Including Self-Contained Acoustic Fault Detection Apparatus." See, also, U.S. Pat. No. 7,142,911 to Boileau et al., entitled "Method and Apparatus for Monitoring Drug Effects on Cardiac Electrical Signals using an Implantable Cardiac Stimulation Device." In other embodiments, information pertaining to pulmonary congestion is transmitted to an external system 16, which generates diagnostic displays instructing the patient (directly or via a caregiver) to take certain dosages of diuretics or other medications. External system 16 may include, for example, an external programmer, bedside monitor or hand-held personal advisory module (PAM). Data from the external system can be forwarded to a centralized system such as the Merlin.Net system, the HouseCall™ remote monitoring system or the Merlin@home systems of St. Jude Medical for notifying the clinician of a pulmonary fluid overload within the patient.

Warnings as to pulmonary congestion or edema may also be generated using the bedside monitor, PAM, or an internal warning device provided within the pacer/CRT. The internal warning device can be a vibrating device or a "tickle" voltage device that, in either case, provides perceptible stimulation to the patient to alert the patient. (Again, see Lord et al.) The bedside monitor or PAM can provide audible or visual alarm signals to alert the patient or caregiver, as well as appropriate textual or graphic displays. In addition, diagnostic information pertaining to pulmonary congestion (and to any medical conditions detected therefrom) may be stored within the pacer/CRT for subsequent transmission to an external programmer for review by a clinician during a follow-up session between patient and clinician. The clinician then prescribes any other appropriate therapies to address the condition. The clinician may also adjust the operation of the pacer/CRT to activate, deactivate or otherwise control any therapies provided.

Additionally, the pacer/CRT can perform a wide variety of pacing and/or defibrillation functions such as delivering pacing in response to an arrhythmia or generating and delivering shocks in response to fibrillation. As a pacer/CRT, the device is also equipped to deliver and control CRT. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT is discussed, for example, in U.S. Pat. No. 8,019,409 to Rosenberg et al., entitled "Cardiac Resynchronization Therapy Optimization using Electromechanical Delay from Realtime Electrode Motion Tracking."

Note that systems provided in accordance with the invention need not include all the components shown in FIG. 1. In many cases, for example, the implantable system will include only the pacer/CRT and its leads. Drug pumps are not necessarily employed. Some implementations may employ an external monitor for generating warning signals but no internal warning device. These are just a few exemplary embodiments. No attempt is made herein to describe all possible combinations of components that may be provided in accordance with the general principles of the invention. Also, note that, although internal signal transmission lines are shown in FIG. 1 for interconnecting implanted components, wireless signal transmission might alternatively be employed where appropriate. In addition, it should be understood that the particular shape, size and locations of the implanted components shown in FIG. 1 are merely illustrative and may not necessarily correspond to actual implant locations. Exemplary implant locations for the leads are more precisely illustrated in FIG. 9.

RV/LV Stroke Volume-Based Pulmonary Congestion/Edema Detection

Figure 2:
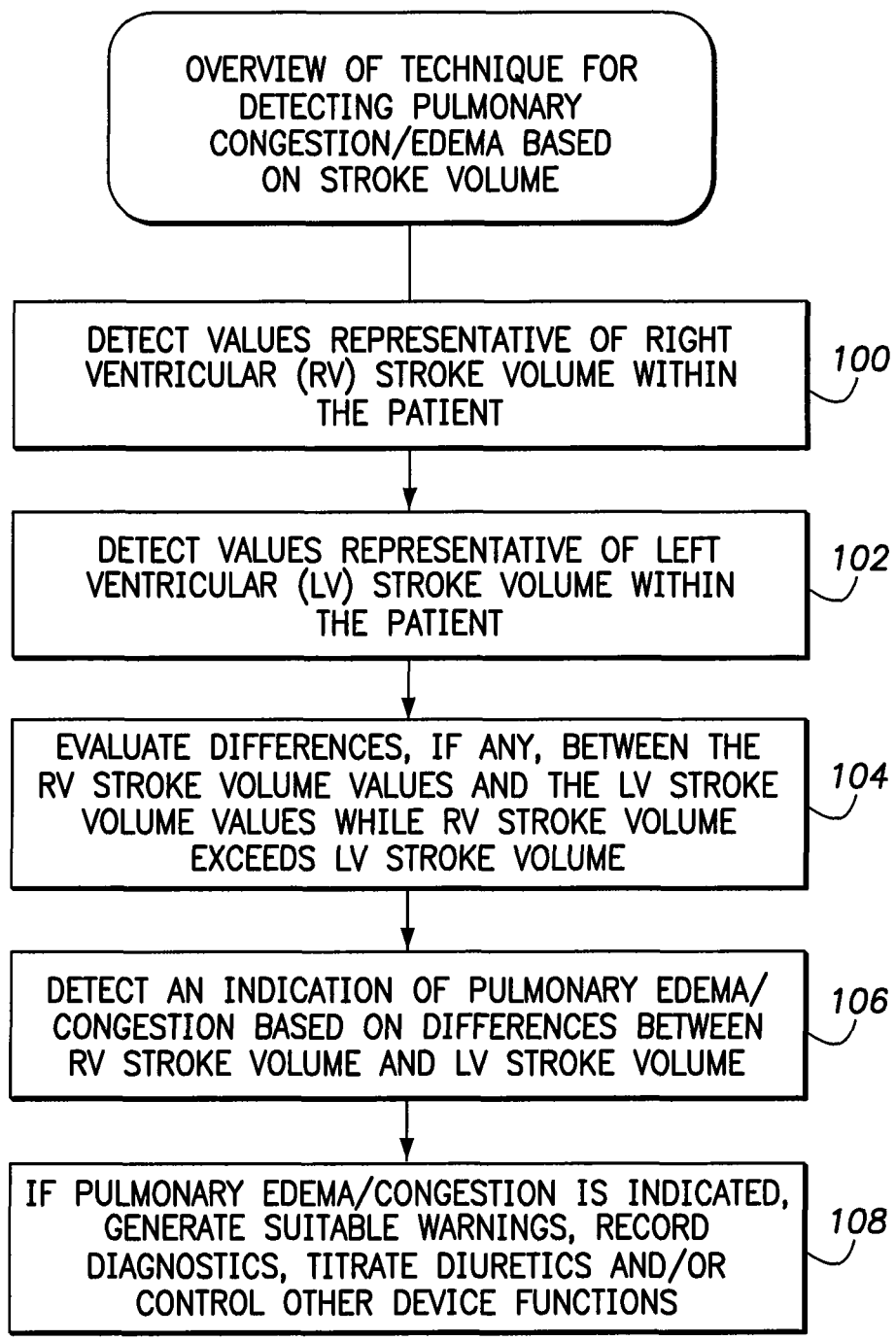
FIG. 2 summarizes a stroke volume-based technique for detecting pulmonary congestion, which may be performed by the system of FIG. 1.

FIG. 2 broadly summarizes general techniques for detecting pulmonary fluid congestion that may be exploited by the pacer/CRT of FIG. 1 or other suitably equipped systems. Beginning at step 100, the pacer/CRT detects values representative of RV stroke volume within the patient based, for example, on pulmonary artery pressure measurements or certain intracardiac impedance measurement to be described in detail below. At step 102, the device detects values representative of LV stroke volume based, for example, on aortic pressure measurements, LAP measurements or certain extracardiac impedance measurements, also to be described in detail below. At step 104, the device evaluates differences, if any, between RV stroke volume and LV stroke volume, at least during periods of time while RV stroke volume exceeds LV stroke volume. For example, the device may generate an edema index (which may also be referred to as a pulmonary congestion index) based on an accumulated difference between RV stroke volume and the LV stroke volume values during periods of time when RV stroke volume exceeds LV stroke volume by at least a minimal amount using techniques discussed below. At step 106, the device detects an indication of pulmonary edema and/or pulmonary congestion based on differences between RV stroke volume and LV stroke volume by, for example, comparing the edema index against a suitable threshold. At step 108, if pulmonary edema/congestion is indicated, the device generates alarms or warnings, records suitable diagnostics, titrates diuretics and/or controls any other device functions. The other device functions to be controlled can comprise any appropriate function that can be performed or controlled by the device (alone or in combination with other devices) such as detecting and trending heart failure related medical conditions. Note that titration of decongestive therapies is discussed in: U.S. Patent Application 2008/0294209 of Thompson et al., entitled "Decongestive Therapy Titration for Heart Failure Patients using Implantable Sensor."

Figures 1, 3:
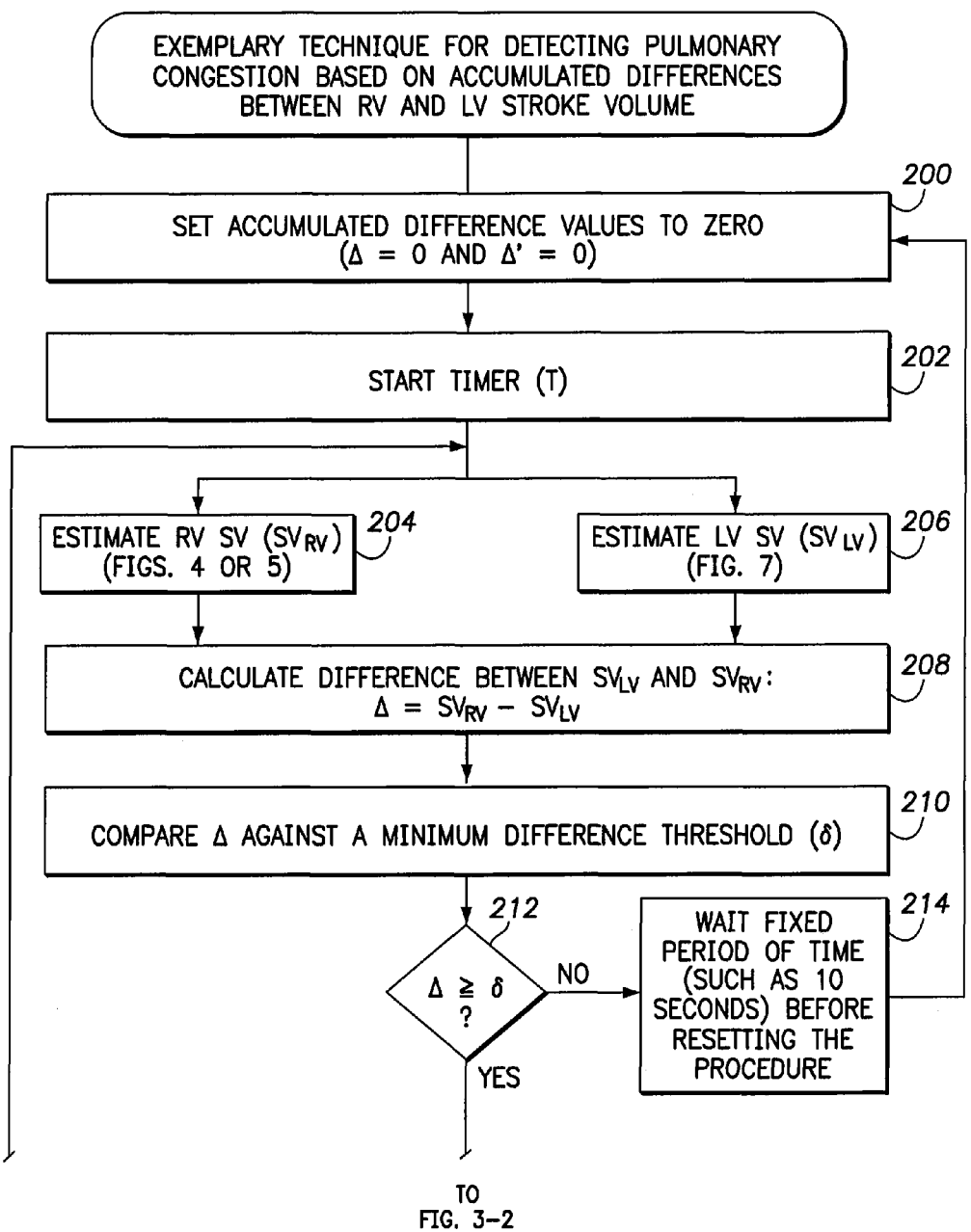
FIG. 3 illustrates an exemplary embodiment of the stroke volume-based technique of FIG. 2 where an edema index is tracked.
Figures 2, 3:
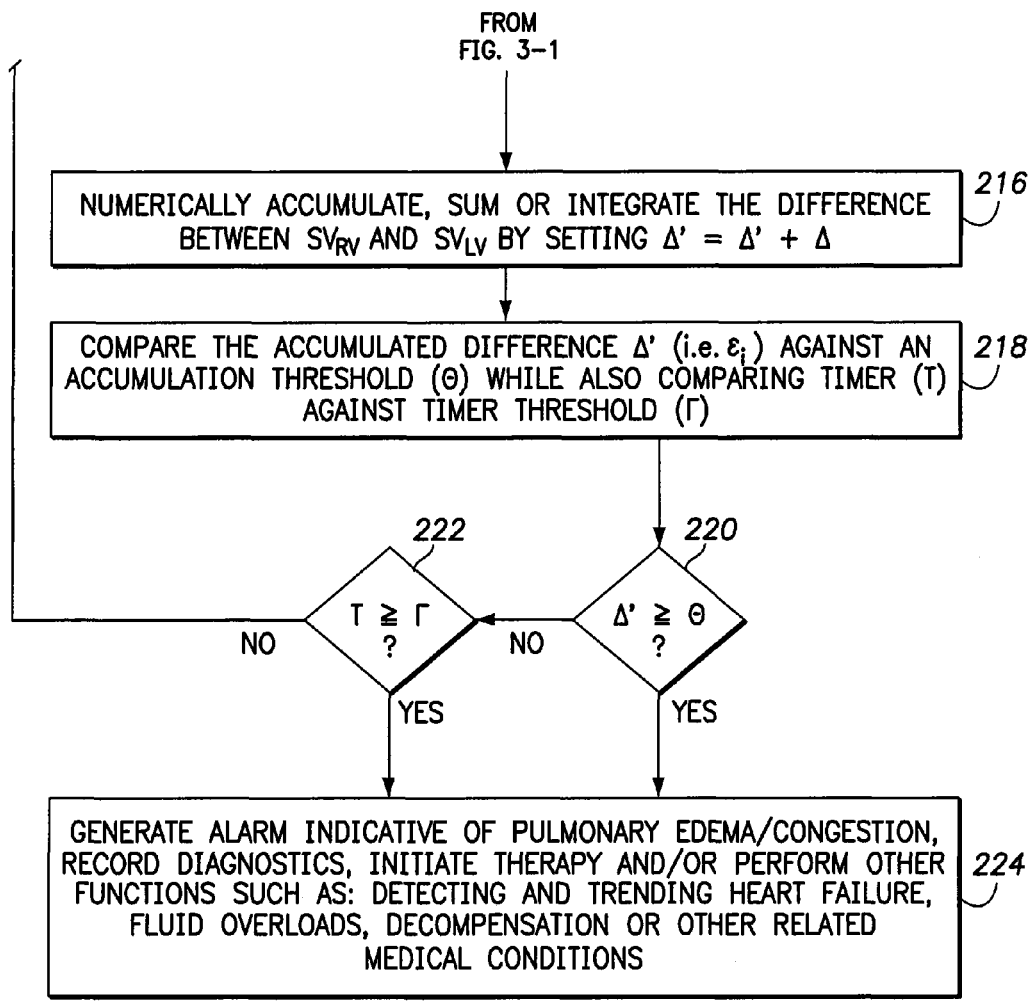

FIG. 3 illustrates an exemplary technique for detecting pulmonary congestion based on accumulated differences between RV and LV stroke volume quantified by an edema index. At step 200, the pacer/CRT sets a pair of accumulated difference values to zero: $\Delta=0$ and $\Delta'=0$. These values will be used to sum the difference between RV and LV stroke volume. At step 202, the device starts a timer (T) for tracking the interval of time that RV stroke volume exceeds LV stroke volume by at least a minimal amount. At step 204, the device determines or estimates the current RV stroke volume ($SV_{RV}$) for the patient using the techniques of FIG. 4 or 5. Concurrently, at step 206, the device also determines or estimates the current LV stroke volume ($SV_{LV}$) using the techniques of FIG. 7. At step 208, the device calculates the difference between the most recent values for $SV_{LV}$ and $SV_{RV}$: $\Delta=SV_{RV}-SV_{LV}$. At step 210, the device compares $\Delta$ against a minimum difference threshold ($\delta$) or "noise limit" provided to ensure that the edema index is only calculated during periods of time when the RV stroke volume exceeds the LV stroke volume by at least the aforementioned minimal amount. This helps ensure that small or minute elevations in RV stroke volume over LV stroke volume arising due to signal noise, normal variability in stroke volumes or other non-clinically significant factors are properly ignored. At 212, if $\Delta$ is less than $\delta$, the device at step 214 waits a fixed period of time X (such as ten seconds) before returning to step 200 to reset the procedure. Appropriate values for X and $\delta$ may be preprogrammed into the device or set or adjusted by the clinician during a post-implant follow-up session with the patient. The appropriate value to be used for $\delta$ may depend on the magnitude of the stroke volume within the particular patient and the amount of natural variation in that stroke volume. In one example, a suitable value for $\delta$ might be 3-5 ml. In this regard, if stroke volume for these heart failure patients is assumed to be slightly reduced from the normal (e.g., reduced from 70-80 ml to 60 ml), then a difference of more than 5% (i.e. 3 ml) should be considered above the noise level, yielding the aforementioned 3-5 ml exemplary value. Other suitable values may be obtained through clinical trials or human feasibility studies.

At 212, assuming that $\Delta$ is greater than or equal to $\delta$, indicating that RV stroke volume exceeds the LV stroke volume by at least a minimally significant amount, the device then begins accumulating differences between RV stroke volume and LV stroke volume. That is, at step 216, the device numerically accumulates, sums or integrates the difference between $SV_{RV}$ and $SV_{LV}$ by setting $\Delta'=\Delta'+\Delta$. (As noted above, the accumulated value $\Delta'$ may also be referred to as an edema index $\epsilon_i$.) During a first iteration or "lap" of the procedure, $\Delta'$ is set equal to $\Delta$ since $\Delta'$ is initially zero. During subsequent iterations, $\Delta'$ will accumulate the numerical difference between RV and LV stroke volumes. Following each new calculation of $\Delta'$ at step 216, the device at step 218 compares the accumulated difference ($\Delta'$) against an accumulation threshold ($\Theta$) while also comparing timer (T) against a timer threshold ($\Gamma$). Note that the accumulated value $\Delta'$ may also be referred to as an edema index $\epsilon_i$. So long as $\Delta'$ (i.e. $\epsilon_i$) remains below $\Theta$ (as determined at step 220) and the timer T remains less than $\Gamma$ (as determined at step 222), the device periodically returns to steps 204 and 206 to update the values for $SV_{RV}$ and $SV_{LV}$ and accumulate further differences between $SV_{RV}$ and $SV_{RV}$ (so long as the latest value for $\Delta$ is greater than or equal to $\delta$.) The main processing loop represented by steps 204/206 through 220/222 may be repeated for example, once every second hour or once every fourth hour, subject to device programming. During any particular iteration of the main loop, if $\Delta'$ reaches the accumulation threshold $\Theta$, the device responds at step 224 by generating an alarm indicative of pulmonary edema/congestion, recording suitable diagnostics and/or initiating therapy such as delivery of diuretics. At step 224, the device can also initiate or perform other functions such as: detecting and trending heart failure, fluid overloads, decompensation, or other related medical conditions. Likewise, if the timer reaches timer threshold $\Gamma$ at step 222, indicating that the patient has remained in a state of elevated RV stroke volume (relative to LV stroke volume), the same or similar actions are taken at step 224.

As with the minimum difference threshold ($\delta$), an appropriate value for the accumulation threshold ($\Theta$) may be preprogrammed into the device (based on the results of clinical trials) or set or adjusted by the clinician during a post-implant follow up session with the patient. The actual value to be used may depend on the magnitude of the stroke volume within the particular patient and the amount of natural variation in stroke volume. In one example, a suitable value for $\Theta$ might be 100 ml. Likewise, the timer threshold $\Gamma$ may be preprogrammed into the device (based on the results of clinical trials) or set or adjusted by the clinician during a follow up session with the patient. In one example, if the accumulation threshold is 100 ml, a suitable value for $\Gamma$ might be twenty-four hours. Preferably, the parameters are set in conjunction with one another. For example, if an accumulated difference ($\Theta$) of 200 ml is achieved in twenty-four hours, the patient will most likely be very sick acutely. Over a period of months, the lungs can harbor several liters of fluid. With an accumulation threshold of 100 ml, a time constant of twenty-four hours may therefore be appropriate, whereas a time constant of thirty days may be preferred if the accumulated difference should increase to 500 ml. These values may be set by the clinician based on the pathophysiology of the patient and the severity of his or her disease. For a very sick New York Heart Association (NYHA) IIIb/IV patient with diastolic dysfunction, a short and tight setting is preferably programmed. However, for a healthier patient, e.g. NYHA who does not have any previous arrhythmia nor diastolic dysfunction, a timeline of, e.g., one to three months is more appropriate.

Figure 6:
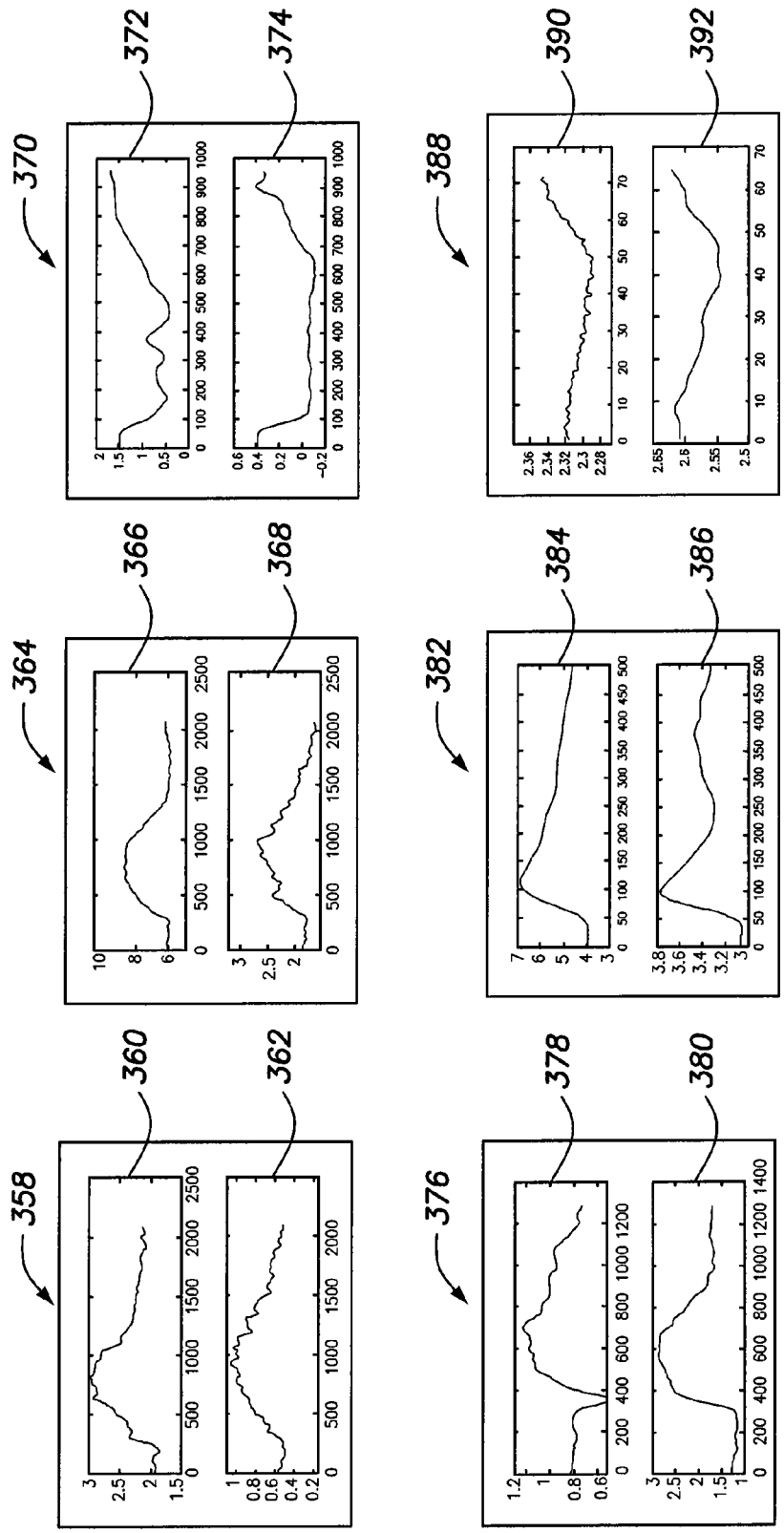
FIG. 6 provides graphs relating intracardiac impedance to RV stroke volume exploited by the technique of FIG. 5.

Although not shown in FIG. 6, processing ultimately returns to step 200 following the actions taken at step 224 to reset the procedure. This may be done, for example, after the episode of pulmonary congestion has been resolved.

Note that if the device is equipped with other pulmonary edema detection systems, such systems may be used to corroborate the detection of possible pulmonary edema/congestion made at step 224 before alarms are generated or therapy is initiated. See, for example, techniques described in U.S. Patent Application 2011/0125049 of Nabutovsky et al., entitled "Methods and Systems that Use Implanted Posture Sensor to Monitor Pulmonary Edema" and U.S. Patent Application 2010/0106210 of Hedberg et al., entitled "Implantable Medical System for Detecting Incipient Edema." See, also, techniques discussed in U.S. Pat. No. 7,272,443 to Min et al., entitled "System and Method for Predicting a Heart Condition based on Impedance Values using an Implantable Medical Device"; U.S. Pat. No. 8,032,212 of Bornzin et al., entitled "System and Method for Monitoring Thoracic Fluid Levels Based on Impedance Using an Implantable Medical Device"; U.S. Pat. No. 7,628,757 to Koh, entitled "System and Method for Impedance-Based Detection of Pulmonary Edema and Reduced Respiration using an Implantable Medical System"; and U.S. Patent Application 2010/0305641 of Pillai et al., entitled "System and Method for Detecting Pulmonary Edema based on Impedance Measured using an Implantable Medical Device during a Lead Maturation Interval." See, also, U.S. Pat. No. 7,272,443, of Min et al., entitled "System and Method for Predicting a Heart Condition based on Impedance Values using an Implantable Medical Device" and U.S. Pat. No. 7,917,194 to Reed et al., entitled "Method and Apparatus for Detecting Pulmonary Edema."

Insofar as the detection or trending of heart failure, fluid overloads or decompensation is concerned, see techniques discussed in: U.S. Patent Application 2011/0184301 of Holmstrom et al., entitled "Heart Failure Detector"; U.S. Patent Application 2011/0144508 of Blomqvist et al., entitled "Method and Device for Monitoring Acute Decompensated Heart Failure"; and U.S. Patent Application 2011/0028855 of Blomqvist, entitled "Heart Failure Detecting Medical Device." See, also, techniques discussed in: U.S. Pat. No. 6,748,261, entitled "Implantable Cardiac Stimulation Device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable Cardiac Stimulation Device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure."

Figure 4:
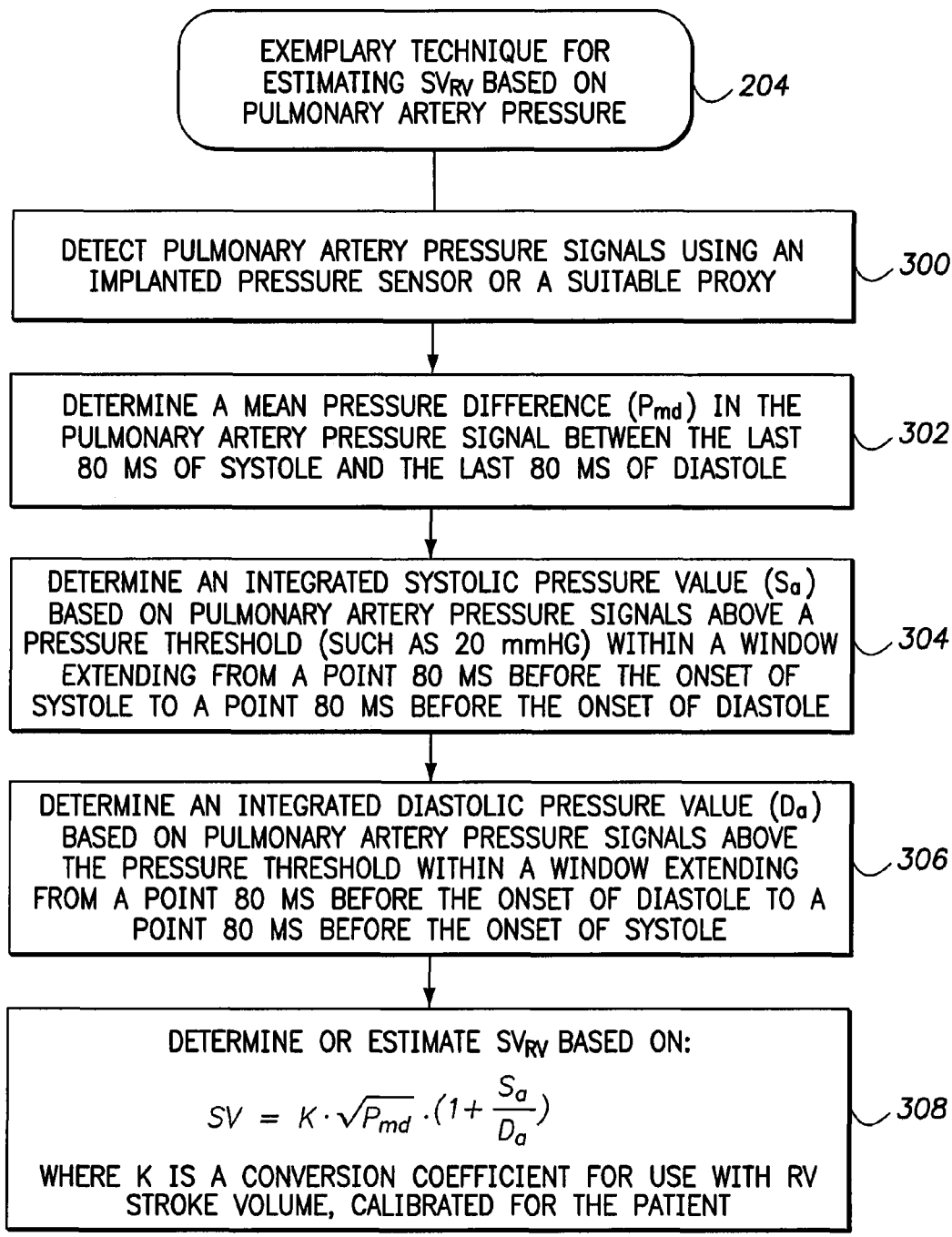
FIG. 4 illustrates an exemplary technique for determining RV stroke volume based on pulmonary artery pressure for use with the technique of FIG. 3.

FIG. 4 illustrates an exemplary technique for use at step 204 of FIG. 3 for estimating RV stroke volume based on pulmonary artery pressure. At step 300, the pacer/CRT detects pulmonary arterial pressure signals using an implanted pressure sensor or a suitable proxy. Sensors for use in the pulmonary artery are discussed, for example, in U.S. Pat. No. 7,621,036 of Cros et al., entitled "Method of Manufacturing Implantable Wireless Sensor for In Vivo Pressure Measurement," U.S. Published Patent Application 2006/0287602 of O'Brien et al., entitled "Implantable Wireless Sensor for In Vivo Pressure Measurement," and U.S. Pat. No. 8,021,307 to White et al., entitled "Apparatus and Method for Sensor Deployment and Fixation," each initially assigned to CardioMems, Inc. See, also, techniques discussed in U.S. Patent Application 2010/0286535 of Blomqvist, entitled "Medical Device for Detecting Pulmonary Artery Pressure." At step 302, the device determines a mean pressure difference ($P_{md}$) in the pulmonary artery pressure signal between the last 80 ms of systole and the last 80 ms of diastole (or within other suitable time windows or intervals.) The systolic and diastolic intervals can be detected using conventional techniques. At step 304, the device determines an integrated systolic pressure value ($S_a$) based on pulmonary artery pressure signals above a pressure threshold (such as 20 mmHg) within a window extending from a point 80 ms before the onset of systole to a point 80 ms before the onset of diastole (or within other suitable time windows or intervals.) $S_A$ may be calculated, for example, by digitizing the pulmonary pressure signals within that interval and then numerically integrating the digitized values using otherwise conventional techniques. At step 306, the device also determines an integrated diastolic pressure value ($D_a$) based on pulmonary artery pressure signals above the 20 mmHg pressure threshold within a window extending from a point 80 ms before the onset of diastole to a point 80 ms before the onset of systole. At step 308, the device then calculates or determines the current RV stroke volume based on:

$$SV = K \cdot \sqrt{P_{md}} \cdot \left(1 + \frac{S_a}{D_a}\right)$$

where K is a predetermined conversion coefficient or conversion factor that has been calibrated to relate the value generated by the formula to RV stroke volume within the patient. The value for K may be calibrated, for example, during a post-implant follow up session by using echocardiography to measure RV stroke volume within the patient while the parameters for $S_a$, $D_a$ and $P_{md}$ are also determined. Note that this formula is referred to as the Warner formula. See Alderman et al., "Evaluation of the Pulse-Contour Method of Determining Stroke Volume in Man," Circulation 1972; 46:546. Other suitable formulas might be appropriate as well. In general, any formula that reliably and accurately estimates RV stroke volume within the patient based on $S_a$, $D_a$ and $P_{md}$ can be employed.

Figure 5:
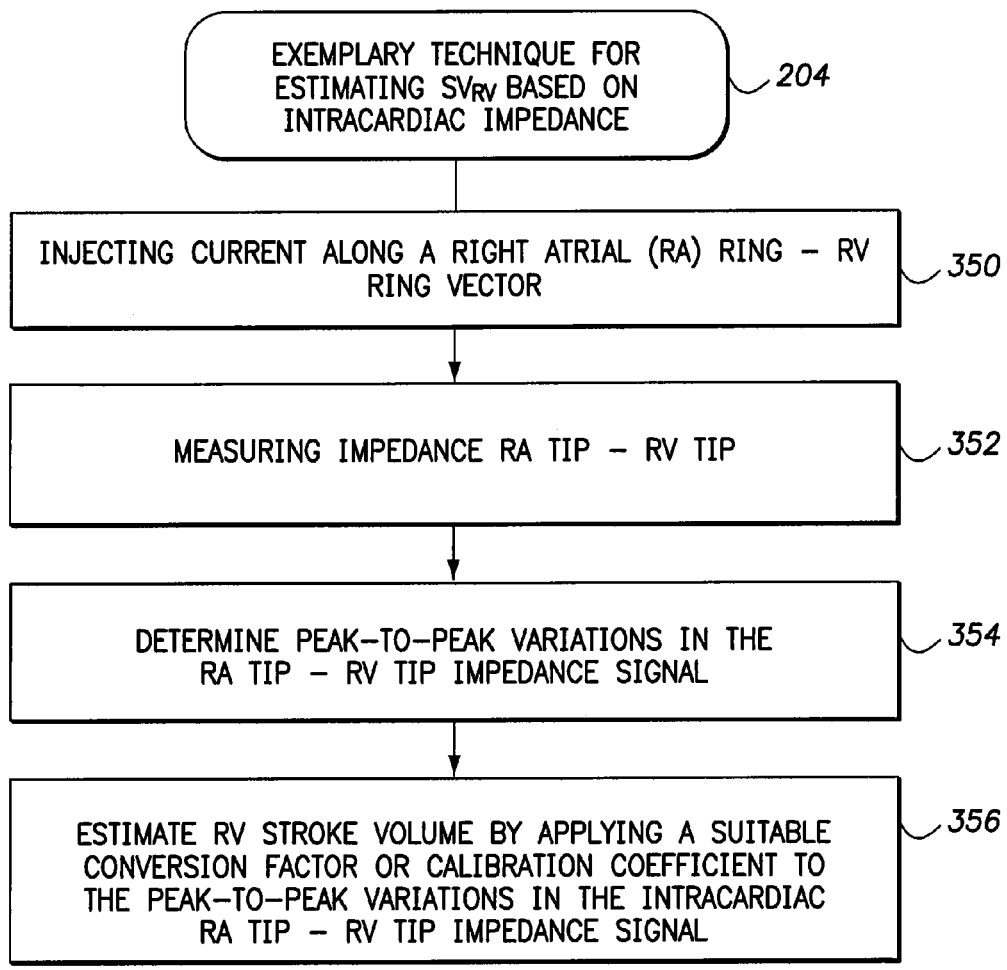
FIG. 5 illustrates an exemplary technique for determining RV stroke volume based on intracardiac impedance for use with the technique of FIG. 3.

FIG. 5 illustrates an alternative technique for use at step 204 of FIG. 3 for estimating RV stroke volume, which is based on intracardiac impedance. At step 350, the pacer/CRT injects current along a right atrial (RA) ring—RV ring vector for the purposes of impedance measurement. At step 352, the device measures values representative of impedance along an RA tip—RV tip vector. Hence, a different vector is used for measuring impedance as compared to the vector employed for injecting the current. This is a quadropolar impedance configuration. Note that, insofar as impedance is concerned, it should be understood that related electrical parameters might be detected and/or exploited instead, such as admittance, conductance or immittance. Those skilled in the art can convert among these related parameters where appropriate. Herein, "values representative of impedance" is intended to generally include related electrical parameters. At step 354, the device determines peak-to-peak variations in the RA tip—RV tip impedance signal (filtered if warranted.) That is, within each cardiac cycle, the device detects a maximum peak (highest amplitude value) and a minimum peak (i.e. the lowest amplitude value or trough) with the impedance signal and determines the magnitude of the difference therebetween, which is the peak-to-peak variation. At step 356, the device then estimates RV stroke volume by applying a conversion factor or calibration coefficient to the peak-to-peak variation in the measured impedance. The calibration constant is set to relate the peak-to-peak variation to RV stroke volume within the patient. The coefficient may be calibrated, for example, post-implant using echocardiography to measure RV stroke volume within the patient while the peak-to-peak impedance variation is also measured.

FIG. 6 provides a set of graphs illustrating peak-to-peak impedance values and corresponding reference stroke volumes derived from animal studies where stroke volume was artificially elevated. In each graph, the impedance values represent filtered quadropolar peak-to-peak impedance values representative of RV stroke volume and derived using the aforementioned injection and measurement vectors. The reference stroke volumes in these examples are LV stroke volumes determined using a flow probe. Note that for healthy subjects, LV and RV stroke volumes are typically quite similar (except for a slight time shift.)

More specifically, first graph 358 shows peak-to-peak impedance 360 in comparison with the reference stroke volume 362 within a porcine test subject where dobutamine infusion was used to induce heart failure and pulmonary edema, resulting in an increase in RV stroke volume. Second graph 364 shows peak-to-peak impedance 366 in comparison with the reference stroke volume 368 within a different porcine test subject where a dobutamine infusion was also employed. Third graph 370 shows peak-to-peak impedance 372 in comparison with the reference stroke volume 374 within a porcine test subject where a pulmonary artery occlusion was applied. A fourth graph 376 shows peak-to-peak impedance 378 in comparison with the reference stroke volume 380 within yet another porcine test subject where a dobutamine infusion was employed. A fifth graph 382 shows peak-to-peak impedance 384 in comparison with the reference stroke volume 386 within still yet another porcine test subject where a dobutamine infusion was employed. Finally, sixth graph 388 shows peak-to-peak impedance 390 in comparison with the reference stroke volume 392 within a porcine test subject where an injection of microspheres (Sephadex™) was employed to cause ischemia. As can be seen, in each case there is good correlation between peak-to-peak impedance and the reference stroke volume as stroke volume varies within the animal test subjects, indicating that the quadropolar peak-to-peak impedance values should permit reliable estimation of stroke volume within human patients (subject to suitable conversion or calibration coefficients.) Note that, if the pacer/CRT is equipped with a pulmonary artery pressure sensor, as well as a quadropole impedance measurement system, the device can estimate RV stroke volume using both techniques to improve the reliability and specificity of the RV stroke volume assessment.

Figure 7:
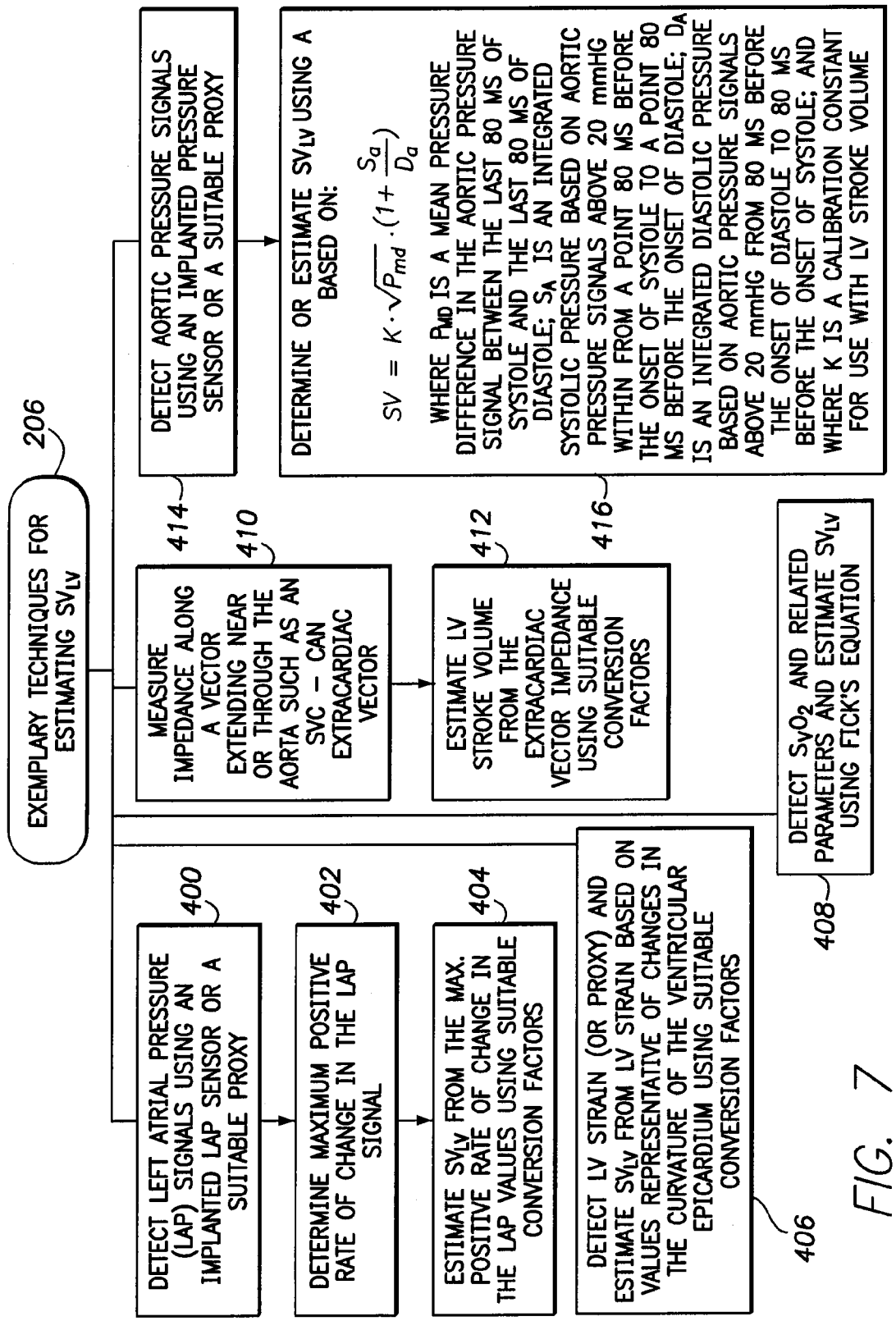
FIG. 7 illustrates exemplary techniques for determining LV stroke volume for use with the technique of FIG. 3.

FIG. 7 illustrates various exemplary techniques for use at step 206 of FIG. 3 for estimating LV stroke volume based on LAP, LV strain or other parameters. These techniques may be used alone or in combination. At step 400, to estimate LV stroke volume based on LAP, the pacer/CRT detects LAP signals using an implanted LAP sensor (if so equipped) or a suitable proxy. LAP sensors and suitable locations for mounting such sensors are discussed in, for example, U.S. Pat. No. 7,115,095 of Eigler et al., entitled "Permanently Implantable System and Method for Detecting, Diagnosing and Treating Congestive Heart Failure." See, also, U.S. patent application Ser. No. 11/856,443, filed Sep. 17, 2007, of Zhao et al., entitled "MEMS-Based Left Atrial Pressure Sensor for use with an Implantable Medical Device," U.S. Patent Application 2011/0125207 of Nabutovsky et al., entitled "Methods and Systems that use Implanted Posture Sensor to Monitor Left Atrial Pressure and/or Inter-Thoracic Fluid Volume"; and U.S. Patent Application 2011/0208077 of Soriano et al., entitled "System and Method for Exploiting Atrial Electrocardiac Parameters in Assessing Left Atrial Pressure using an Implantable Medical Device." At step 402, the device determines a maximum positive rate of change in the LAP signal and, at step 404, estimates $SV_{LV}$ from the maximum positive rate of change in the LAP values using suitable conversion factors calibrated for the patient. Such conversion factors may be calibrated, for example, post-implant using echocardiography to measure LV stroke volume within the patient while the LAP is also measured.

Further with regard to LAP, in an internal zLAP CRT study (not yet published), the echo parameter left ventricular outflow tract velocity time integral (LVOT VTI) was used to optimize atrioventricular delays (AVD) and interventricular delays (VVD) for eight heart failure patients. A continuous LAP signal was parameterized for use as a means for optimizing AVD/VVD. The best parameterization was identified as the maximum positive rate of change of the LAP. The AVD and VVD values identified as optimal using the LAP-based technique were compared to the AVD and VVD values identified using LVOT VTI for each patient to thereby evaluate the performance of the LAP based optimization. These differences on a population level were: −11.4±36.7 ms (AVD) and −3.6±25.1 ms (VVD). This indicates that the preferred LAP parameterization (i.e. maximum positive rate of change in LAP) correlates well with LVOT VTI, which in turn is intimately connected to stroke volume, confirming that the maximum positive rate of change in LAP may permit estimation of LV stroke volume subject to suitable conversion or calibration coefficients.

At step 406, the pacer/CRT instead detects LV strain (if equipped with a suitable sensor or proxy) and estimates $SV_{LV}$ from the LV strain based on values representative of changes in the curvature of the ventricular epicardium using suitable conversion factors calibrated for the patient. Such conversion factors may be calibrated, for example, post-implant using echocardiography to measure LV stroke volume within the patient while LA strain is also measured. LV strain is discussed in U.S. Pat. No. 7,805,194 to Schecter, entitled "Matrix Optimization Method of Individually Adapting Therapy in an Implantable Cardiac Therapy Device." See, also, techniques for assessing the shape of the LV discussed in U.S. patent application Ser. No. 12/975,085, filed Dec. 21, 2010, of Rosenberg et al., entitled "Systems and Methods for Assessing the Sphericity and Dimensional Extent of Heart Chambers for use with an Implantable Medical Device." See, also, U.S. Patent Application 2010/0030087 of Hettrick et al., entitled "Estimating Cardiovascular Pressure and Volume Using Impedance Measurements."

At step 408, the pacer/CRT detects $S_vO_2$ and related parameters and estimates $SV_{LV}$ using Fick's principle. Techniques for detecting blood oxygen saturation values are discussed in U.S. Pat. No. 8,099,146, of Koh, entitled "System and Method for Calibrating a Blood Oxygen Saturation Sensor for use with an Implantable Medical Device." In one example, the device estimates $SV_{LV}$ using based on $S_vO_2$ using Fick's principle, which relates oxygen uptake ($VO_2$), hemoglobin (Hb), arterial oxygen saturation ($SaO_2$) and $S_vO_2$ to cardiac output (Q). In one example, Hb is assumed to be constant and $SaO_2$ and $S_vO_2$ are measured or estimated using existing sensors/technology. Then, assuming that the arterial oxygenation is 100% (a valid assumption unless the patient has any severe lung disease), the device assesses the returning blood to the right atrium using $SvO_2$. In this manner, the device can assess the large circulatory system and not the pulmonary system and hence can estimate LV stroke volume ($SV_{LV}$.)

At step 410, the pacer/CRT instead measures impedance along an extracardiac vector extending through the aorta such as an SVC—can vector. This is referred to herein as an extracardiac vector since at least a portion of the vector extends beyond the heart. At step 412, the device estimates LV stroke volume from the extracardiac vector impedance using suitable conversion factors by, for example, exploiting the peak-to-peak amplitude of the SVC-Can vector. The principle behind this technique is that the extra-cardiac impedance vector measures across (or spans) the base of the aorta so that aortic pulsations can provide a source of stroke volume information via the measured impedance signal. See, techniques described in U.S. Pat. No. 7,925,348 of Bornzin et al., entitled "Extra-cardiac Impedance based Hemodynamic Assessment Method and System" that assess cardiac output and stroke volume from SVC-based impedance vectors. Note that other vectors besides the SVC coil-can vector may instead be employed for measuring impedance through the aorta, such as a vector between an LV electrode and an extracardiac electrode mounted away from the heart along the SVC and positioned such that a substantial portion of the vector passes along the aorta. Again, see U.S. Pat. No. 7,925,348, particularly FIG. 1 of that document. Also, see the graphs of FIG. 15 of that document, which show Z area, cardiac output and other parameters such as AV delays. Internal studies (unpublished) have shown that the bipolar, extra-cardiac impedance vector SVC-Can can be used to estimate left ventricular stroke volume and cardiac output.

The device can also exploit aortic pressure signals (if the device is equipped to obtain such signals) to estimate LV stroke volume using techniques similar to those already described for estimating RV stroke volume from pulmonary artery pressure. That is, at step 414, the device detects aortic pressure signals using an implanted pressure sensor or a suitable proxy. See, for example, techniques described in U.S. Pat. No. 7,654,964, of Kroll et al., entitled "System and Method for Detecting Arterial Blood Pressure based on Aortic Electrical Resistance using an Implantable Medical Device." See, also, U.S. Pat. No. 7,139,609 to Min et al., entitled "System and Method for Monitoring Cardiac Function via Cardiac Sounds using an Implantable Cardiac Stimulation Device" and U.S. Patent Application 2010/0113944 to Min et al., entitled "Interpolating Left Ventricular Pressures." At step 416, the device determines or estimates LV stroke volume using the formula shown above, but modified (where appropriate) to address aortic pressures and LV stroke volume. In one example, PMD is a mean pressure difference in the aortic pressure signal between the last 80 ms of systole and the last 80 ms of diastole; SA is an integrated systolic pressure based on aortic pressure signals above 20 mmHG within from a point 80 ms before the onset of systole to a point 80 ms before the onset of diastole; DA is an integrated diastolic pressure based on aortic pressure signals above 20 mmHG from 80 ms before the onset of diastole to 80 ms before the onset of systole. (In this regard, the difference between LVP and Aortic pressure (AP) is that LVP starts from zero. If the device obtains its measurements after the opening of the aortic valve, then the two curves overlap and so the parameters discussed above in connection with FIG. 4 can also be used, e.g. 80 ms intervals, a 20 mmHg threshold, etc.) The calibration value (K) to be used in the modified formula differs from the one used for RV stroke volume and can be calibrated post-implant using echocardiography to measure LV stroke volume within the patient while aortic pressure is also determined. Other suitable formulas might be appropriate as well. In general, any formula that reliably and accurately estimates LV stroke volume within the patient based on aortic pressure can be employed. Note that if the pacer/CRT is equipped to perform two or more of the LV stroke volume estimation techniques of FIG. 7, the results can be merged or averaged as needed to provide an improved estimate.

One advantage of the stroke volume-based methods described herein is that the techniques provide simple and reliable methods for detecting the onset of pulmonary congestion so that appropriate action can be taken to avoid hospitalization of the patient. Moreover, the techniques described herein can provide insight into setting edema "alarms" for immediate clinical action, as well as providing diagnostic information helpful in understanding the patient's hemodynamic reserve. Both applications should be useful to physicians and clinicians who manage heart failure patients in both acute and chronic heart failure management settings. In general, the techniques described herein provide a powerful means for avoiding hospitalization and unnecessary health care cost and suffering.

Although particular processing examples are described herein, it is of course possible to expand these techniques to make the device "smarter" or to add more layers to the analysis. For instance, it may be advantageous to implement device logic that will not only examine RV/LV stroke volume imbalances via the iterative techniques of FIG. 3 but would employ an "outer loop" that also monitors how often per month the procedure is activated. It is conceivable that the device may go through a couple of cycles every now and then but the edema alarm never triggers, either because the severity was not high enough or because the thresholds were programmed too high. It can, however, still have clinical relevance to examine the patient if the procedure stays in active mode several cycles per month even if no alarms are generated.

For the sake of completeness, an exemplary pacer/CRT will now be described, which includes components for performing the functions and steps already described. Although described primarily with respect to an implementation having bipolar leads, aspects of the invention are also generally applicable to systems having multi-pole leads such as a quad-pole LV lead. Also, as noted, extracardiac electrodes may be provided along the SVC away from the heart or at other suitable locations for use in obtaining impedance measurements along particular vectors.

Exemplary Pacer/CRT

FIG. 8 provides a simplified block diagram of an exemplary pacer/CRT, which is a dual-chamber stimulation device capable of treating both fast and slow arrhythmias with stimulation therapy, including cardioversion, defibrillation, and pacing stimulation, as well as capable of performing the pulmonary congestion detection functions described above. To provide atrial chamber pacing stimulation and sensing, pacer/CRT 10 is shown in electrical communication with a heart 512 by way of a right atrial lead 520 having a right atrial (RA) tip electrode 522 and an atrial ring electrode 523 implanted in the atrial appendage. In this example, the RA tip electrode 522 is part of a pressure sensing module 529, which is transseptally implanted to permit LAP signals to be sensed while the RA tip and ring electrodes are used for RA sensing/pacing. See, again, U.S. patent application Ser. No. 11/856,443, filed Sep. 17, 2007, of Zhao et al., entitled "MEMS-Based Left Atrial Pressure Sensor for use with an Implantable Medical Device," which is assigned to the assignee of rights to the present application. This is just one example of an LAP sensor.

Pacer/CRT 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle. In this example, right ventricular lead 330 additionally includes a pulmonary artery extension 531, which includes a pressure sensor 533. Pulmonary artery extension 531 is sized, shaped and configured to position the sensor in the pulmonary artery as shown. Signals representative of pressure detected by the sensor are routed back along pulmonary artery extension 531 to the main portion of right ventricular lead 530 then to the pacer/CRT for processing. This is just one example of a pulmonary artery pressure sensor.

To sense left atrial and ventricular cardiac signals and to provide left chamber pacing therapy, pacer/CRT 10 is coupled to a "coronary sinus" lead 524 designed for placement in the "coronary sinus region" via the coronary sinus os for positioning distal electrodes 525, 526 adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 524 is designed to receive atrial and ventricular cardiac signals and to deliver left ventricular pacing therapy using at least a left ventricular tip electrode 526, left atrial pacing therapy using at least a left atrial ring electrode 527, and shocking therapy using at least a left atrial coil electrode 528. With this configuration, biventricular pacing can be performed. Although only three leads are shown in FIG. 8, it should also be understood that additional stimulation leads (with one or more pacing, sensing and/or shocking electrodes) might be used in order to efficiently and effectively provide pacing stimulation to the left side of the heart or atrial cardioversion and/or defibrillation.

Figure 9:
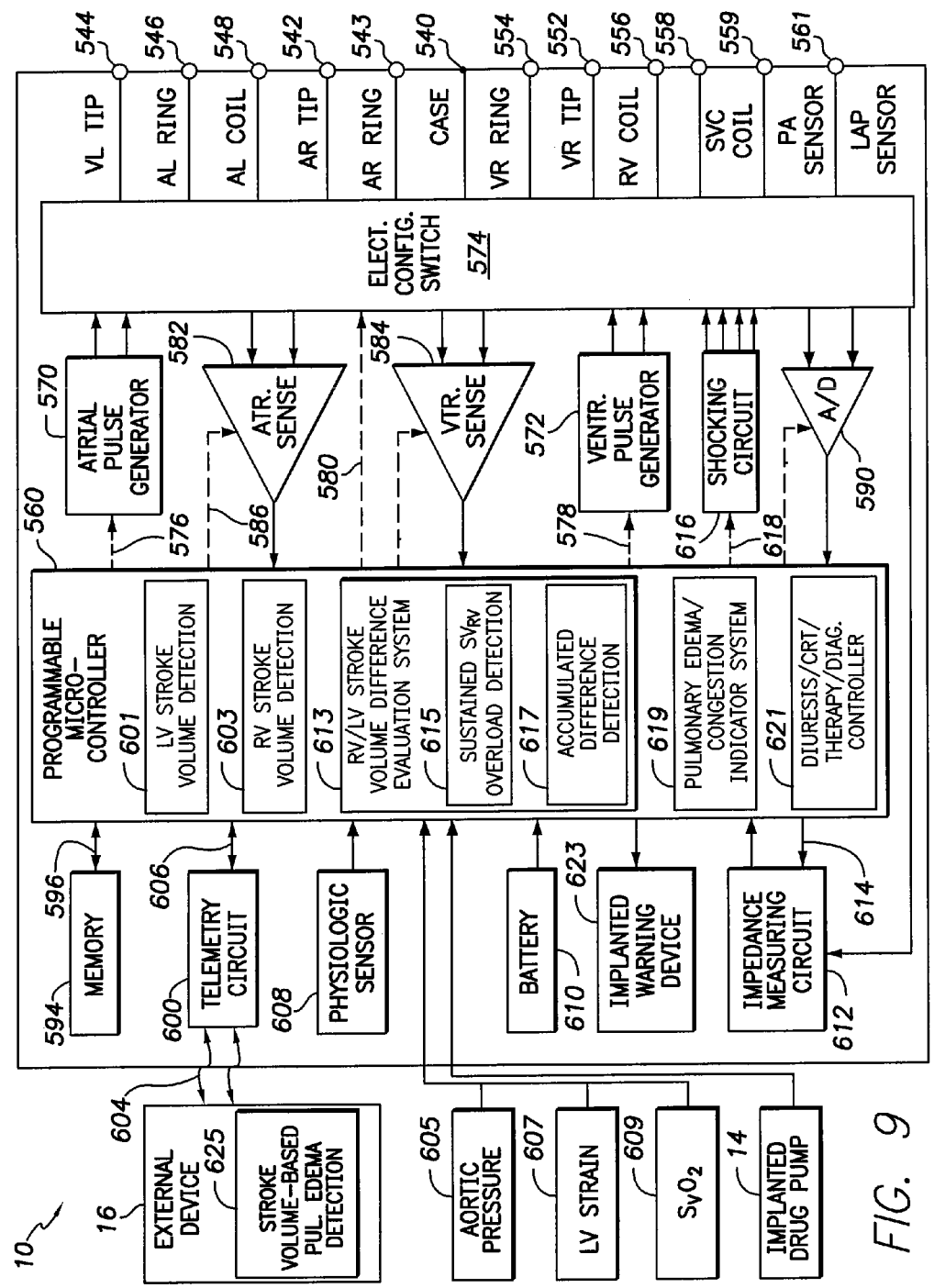
FIG. 9 is a functional block diagram of the pacer/CRT of FIG. 8, illustrating basic circuit elements that provide cardioversion, defibrillation and/or pacing stimulation in the heart and particularly illustrating components for performing or controlling the techniques of FIGS. 2-7.

A simplified block diagram of internal components of pacer/CRT 10 is shown in FIG. 9. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned pulmonary congestion detection functions.

The housing 540 for pacer/CRT 10, shown schematically in FIG. 9, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544, 546, 548, 552, 554, 556, 558, 559 and 561 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes at least a left ventricular tip terminal ($V_L$ TIP) 544, a left atrial ring terminal ($A_L$ RING) 546, and a left atrial shocking terminal ($A_L$ COIL) 548, which are adapted for connection to the left ventricular ring electrode 526, the left atrial tip electrode 527, and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558, which are adapted for connection to the right ventricular tip electrode 532, right ventricular ring electrode 534, the RV coil electrode 536, and the SVC coil electrode 538, respectively. Also, as show, a PA sensor terminal 559 is provided for receiving signals from the PA pressure sensor and an LAP sensor terminal 561 is provided for receiving signals from the LAP pressure sensor. Although not shown, additional terminals may be needed for use with drug dispersing device 14, an LV strain sensor, a $SvO_2$ sensor, an aortic pressure sensor, etc., and for any extracardiac electrodes that might be used.

At the core of pacer/CRT 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 are not critical to the invention. Rather, any suitable microcontroller 560 may be used that carries out the functions described herein. The use of microprocessor-based control circuits for performing timing and data analysis functions are well known in the art.

As shown in FIG. 9, an atrial pulse generator 570 and a ventricular/impedance pulse generator 572 generate pacing stimulation pulses for delivery by the right atrial lead 520, the right ventricular lead 530, and/or the coronary sinus lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, coronary sinus lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/CRT 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/CRT 10 utilizes the atrial and ventricular sensing circuits, 582 and 584, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 590. The data acquisition system 590 is configured to acquire intracardiac electrogram signals, convert the raw analog data into a digital signal, and store the digital signals for later processing and/or telemetric transmission to an external device 16. The data acquisition system 590 is coupled to the right atrial lead 520, the coronary sinus lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/CRT 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/CRT 10 may be non-invasively programmed into the memory 594 through a telemetry circuit 600 in telemetric communication with the external device 16, such as a PAM, bedside monitor, device programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/CRT 10 (as contained in the microcontroller 560 or memory 594) to be sent to the external device 16 through an established communication link 604. Pacer/CRT 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Additionally, sensor 608 could be equipped to detect pulmonary fluid levels or proxies for pulmonary fluid levels. Accordingly, the microcontroller 560 responds by adjusting the various pacing parameters (such as rate, AV Delay, V-V Delay, etc.) at which the atrial and ventricular pulse generators, 570 and 572, generate stimulation pulses. While shown as being included within pacer/CRT 10, it is to be understood that the physiologic sensor 608 may also be external to pacer/CRT 10, yet still be implanted within or carried by the patient. A common type of rate responsive sensor is an activity sensor incorporating an accelerometer or a piezoelectric crystal, which is mounted within the housing 540 of pacer/CRT 10. Other types of physiologic sensors are also known, for example, sensors that sense the oxygen content of the blood, respiration rate and/or minute ventilation, pH of blood, ventricular gradient, etc.

The pacer/CRT additionally includes a battery 610, which provides operating power to all of the circuits shown in FIG. 9. The battery 610 may vary depending on the capabilities of pacer/CRT 10. If the system only provides low voltage therapy, a lithium iodine or lithium copper fluoride cell may be utilized. For pacer/CRT 10, which employs shocking therapy, the battery 610 must be capable of operating at low current drains for long periods, and then be capable of providing high-current pulses (for capacitor charging) when the patient requires a shock pulse. The battery 610 must also have a predictable discharge characteristic so that elective replacement time can be detected. Accordingly, pacer/CRT 10 is preferably capable of high voltage therapy and appropriate batteries are provided.

As further shown in FIG. 9, pacer/CRT 10 also has an impedance measuring circuit 612, which is enabled by the microcontroller 560 via a control signal 614. Herein, impedance is primarily detected for use in measuring intracardiac and extracardiac impedance signals for use in evaluating LV and RV stroke volume. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; detecting the opening of heart valves; as well as detecting the various impedance parameters described above for corroborating fluid overloads, etc. The impedance measuring circuit 612 is advantageously coupled to the switch 574 so that any desired electrode may be used.

In the case where pacer/CRT 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules or more), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules or more), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Microcontroller 560 also includes various components directed to implementing the aforementioned pulmonary congestion detection methods. More specifically, an LV stroke volume detection system 601 is operative to detect values representative of LV stroke volume within the patient and an RV stroke volume detection system 603 is operative to detect values representative of RV stroke volume within the patient. LV and RV stroke volume may be assessed using the techniques described above by exploiting signals from various sensors such as pulmonary artery pressure sensor 533, an aortic pressure sensor 605, an LV strain sensor 607, an $SvO_2$ sensor 609 and an LAP sensor 559, assuming those sensors are provided. Within FIG. 9, some of these sensors are shown schematically. Additional terminals may be needed to receive signals from these devices. As noted, LV and RV stroke volumes can also be assessed based on certain impedance measurements, which may be obtained via impedance circuit 612. The microcontroller further includes an RV/LV stroke volume difference evaluation system 613 operative to evaluate differences between the RV stroke volume values and the LV stroke volume values such as by generating an edema index based on an accumulated difference between the RV and LV stroke volume values. Evaluation system 613 includes a sustained RV stroke volume ($SV_{RV}$) overload detection system 615 operative to track an interval of time during which RV stroke volume exceeds LV stroke volume by at least a minimal amount ($\delta$) and an accumulated difference detection system 617 operative to calculate the accumulated difference between RV and LV stroke volumes during that interval of time. A pulmonary edema/congestion indicator system 619 is operative to detect an indication of pulmonary edema or congestion based on the edema index, using techniques described above.

A diuresis/CRT/therapy/diagnostics controller 621 controls generation of diagnostic data and warning signals in response to pulmonary edema. Diagnostic data is stored within memory 594. Warning signals may be relayed to the patient via implanted warning device 623 or via a bedside monitor, PAM or other external system 16. Controller 617 also controls and titrates the delivery of diuretics (or other appropriate therapies) using drug dispersing device 14 (if one is provided) as described above. In implementations where there is no drug pump, titration of diuretics is typically achieved by instead providing suitable instructions to the patient or caregiver via the bedside monitor (or other external device). If the device is equipped to provide CRT, controller 621 (or other components) may also control the CRT.

Depending upon the implementation, the various components of the microcontroller of the implanted device may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein may be performed by, or under the control of, the external device. Accordingly, external device 16 is shown to include a stroke volume-based pulmonary edema detection system 625 operative to estimate LV and RV stroke volumes based on parameters received from the implanted device, such as pressure measurements or impedance measurements, and to detect pulmonary edema/congestion based on those parameters. In general, any of the components shown within the microcontroller 560 may have corresponding components within the external device.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient, the method comprising:
    detecting values representative of right ventricular (RV) stroke volume within the patient using at least one of a sensor and electrodes;
    detecting values representative of left ventricular (LV) stroke volume within the patient using at least one of the sensor and electrodes;
    evaluating differences, utilizing one or more microcontrollers, between the RV stroke volume values and the LV stroke volume values wherein the evaluating differences include calculating an accumulated difference between the RV stroke volume values and the LV stroke volume values; and
    detecting, utilizing the one or more microcontrollers, an indication of pulmonary congestion based on a comparison between an accumulation threshold and the accumulated difference between the RV stroke volume values and the LV stroke volume values.

2. The method of claim 1 wherein detecting values representative of RV stroke volume within the patient includes detecting pulmonary artery pressure signals using a pressure sensor from the at least one of a sensor and electrodes.

3. The method of claim 2 further including estimating RV stroke volume from the pulmonary artery pressure signals.

4. The method of claim 3 wherein estimating RV stroke volume from the pulmonary artery pressure signals includes calculating:

$$SV = K \cdot \sqrt{P_{md}} \cdot \left(1 + \frac{S_a}{D_a}\right)$$

where SV is the RV stroke volume, $P_{md}$ is a mean pressure difference in pulmonary artery pressure between systole and diastole, $S_a$ is an integrated systolic pressure value based on pressure values above a predetermine pressure and extending over a period of time around systole, $D_a$ is an integrated diastolic pressure value based on pressure values above the predetermine pressure and extending over a period of time around systole, and K is a predetermined calibration constant for use with RV stroke volume.

5. The method of claim 1 wherein detecting values representative of RV stroke volume within the patient includes detecting impedance signals affected by RV stroke volume using electrodes from the at least one of a sensor and electrodes and estimating RV stroke volume from the impedance signals.

6. The method of claim 5 wherein detecting impedance signals and estimating RV stroke volume from the impedance signals includes:
    injecting current along a vector between a right atrial (RA) ring electrode and a RV ring vector;
    measuring impedance along a vector between a RA tip electrode and a RV tip electrode;
    detecting peak-to-peak variations in the measured impedance; and
    converting the peak-to-peak variations to RV stroke volume values using at least one predetermined conversion factor.

7. The method of claim 1 wherein detecting values representative of LV stroke volume within the patient includes detecting impedance signals affected by LV stroke volume using electrodes from the at least one of a sensor and electrodes and estimating LV stroke volume from the impedance signals.

8. The method of claim 7 wherein detecting impedance signals and estimating LV stroke volume from the impedance signals includes:
    measuring impedance along a vector affected by blood flow through the aorta of the patient;
    detecting variations in the measured impedance influenced by LV stroke volume; and
    converting the variations in impedance to LV stroke volume using at least one predetermined conversion factor.

9. The method of claim 8 wherein the vector passing through the aorta of the patient is a vector between a superior vena cava (SVC) coil electrode and a device housing electrode.

10. The method of claim 1 wherein the detecting values representative of LV stroke volume includes detecting values representative of left atrial pressure (LAP) and detecting a maximum positive rate of change in the LAP values.

11. The method of claim 10 further including estimating LV stroke volume from the maximum positive rate of change in the LAP values using at least one predetermined conversion factor.

12. The method of claim 1 wherein the detecting values representative of LV stroke volume includes detecting strain gauge values from an LV strain gauge sensor representative of changes in the curvature of the ventricular epicardium.

13. The method of claim 12 further including estimating LV stroke volume from the strain gauge values using at least one predetermined conversion factor.

14. The method of claim 1 wherein the detecting values representative of LV stroke volume within the patient includes detecting $S_vO_2$ values from an oxygen saturation sensor.

15. The method of claim 14 further including estimating LV stroke volume from the $S_vO_2$ values using at least one predetermined conversion factor.

16. The method of claim 1 wherein the detecting values representative of LV stroke volume within the patient includes detecting aortic pressure signals.

17. The method of claim 16 further including estimating LV stroke volume from the aortic pressure signals.

18. The method of claim 1 wherein the accumulated difference is calculated during an interval of time while the RV stroke volume values exceed the LV stroke volume values.

19. The method of claim 1 wherein calculating the accumulated difference between the RV stroke volume values and the LV stroke volume values includes generating an edema index representative of the accumulated difference while the RV stroke volume values exceed the LV stroke volume values by at least a minimal amount ($\delta$).

20. The method of claim 19 wherein detecting an indication of pulmonary congestion includes comparing the edema index to a threshold ($\Theta$) indicative of pulmonary congestion and generating an indicator signal if the index exceeds the threshold.

21. The method of claim 19 further including:
tracking an interval of time (T) during which the RV stroke volume values exceed the LV stroke volume values by at least a minimal amount ($\delta$); and
comparing the interval of time (T) against a time threshold ($\Gamma$) and generating an indicator signal if the interval of time exceeds the time threshold.

22. The method of claim 1 further including controlling at least one device function in response to the indication of pulmonary congestion including one or more of: recording diagnostics, generating a warming, controlling device therapy, controlling delivery of medications, and detecting and trending heart failure.

23. The method of claim 1 wherein all of the steps are performed by the implantable medical device.

24. The method of claim 1 wherein at least some of the steps are performed by an external device in communication with the implantable medical device.

25. A system for use with an implantable medical device for implant within a patient, the system comprising:
a right ventricular (RV) stroke volume detector comprising at least one of a sensor and electrodes operative to detect values representative of RV stroke volume within the patient;
a left ventricular (LV) stroke volume detector comprising at least one of the sensor and electrodes operative to detect values representative of LV stroke volume within the patient;
an RV/LV stroke volume difference evaluation system operative to calculate an accumulated difference between the RV stroke volume values and the LV stroke volume values; and
a pulmonary congestion indicator system operative to detect an indication of pulmonary congestion based on a comparison between an accumulation threshold and the accumulated difference between the RV stroke volume values and the LV stroke volume values.

26. A system for use with an implantable medical device for implant within a patient, the system comprising:
means for detecting values representative of right ventricular (RV) stroke volume within the patient, the means for detecting comprising at least one of a sensor and electrodes;
means for detecting values representative of left ventricular (LV) stroke volume within the patient, the means for detecting comprising at least one of the sensor and electrodes;
means for calculating an accumulated difference between the RV stroke volume values and the LV stroke volume values; and
means for detecting an indication of pulmonary congestion based on a comparison between an accumulation threshold and the accumulated difference between the RV stroke volume values and the LV stroke volume values.

\* \* \* \* \*